US 6,719,713 B2

(12) United States Patent  (10) Patent No.: US 6,719,713 B2
Mason  (45) Date of Patent: Apr. 13, 2004

(54) STRAP ATTACHMENT ASSEMBLY FOR AN ORTHOPEDIC BRACE (75) Inventor: Jeffrey T. Mason, Escondido, CA (US)

(73) Assignee: Breg, Inc., Vista, CA (US)

( * ) Notice: Subject to any disclaimer, the term of this patent is extended or adjusted under 35 U.S.C. 154(b) by 156 days.

(21) Appl. No.: 10/095,725

(22) Filed: Mar. 14, 2002

(65) Prior Publication Data

US 2003/0176823 A1 Sep. 18, 2003

(51) Int. Cl.[7] .................................................. A61F 5/00
(52) U.S. Cl. .............................. 602/26; 602/5; 602/6; 602/12; 128/869; 128/882; 24/265
(58) Field of Search ........................... 602/26, 5, 6, 12, 602/16, 23; 128/869, 882; 24/265; 224/271

(56) References Cited

U.S. PATENT DOCUMENTS

| 58,403 A | 10/1866 | Goodwin | |
| 732,378 A | 6/1903 | Schopbach | |
| 2,573,866 A | 11/1951 | Murphy | 128/80 |
| 2,636,234 A | * 4/1953 | Reiter | 24/324 |
| 3,387,305 A | 6/1968 | Shafer | 2/22 |
| 3,581,741 A | 6/1971 | Rosman | 128/80 |
| 4,271,999 A | 6/1981 | Stravitz | 224/257 |
| 4,993,127 A | 2/1991 | Mechem et al. | 24/701 |
| 5,572,774 A | 11/1996 | Duren | 24/306 |
| 6,383,156 B1 | * 5/2002 | Enzerink et al. | 602/16 |
| 6,425,166 B1 | * 7/2002 | Seligman et al. | 24/265 AL |
| 2003/0176824 A1 | * 9/2003 | Mason | 602/12 |

* cited by examiner

Primary Examiner—Henry Bennett
Assistant Examiner—Azadeh Kokabi
(74) Attorney, Agent, or Firm—Rodney F. Brown (57) ABSTRACT A strap attachment assembly for an orthopedic brace has an anchor mounted on an orthopedic brace component and a strap retainer mounted on a strap. The anchor has a retention post and a retention head and the strap retainer has a body and a retention plate. The body includes a chamber and the retention plate includes a retention opening aligned with the chamber. The retention opening is sized to releasably receive the retention head when the retention post is positioned in the chamber. The retention plate is transitionable between a locked condition and an unlocked condition. The inner boundary of the retention opening blocks displacement of the retention head therefrom in the locked condition and is clear of the retention head to permit displacement of the retention head therefrom in the unlocked condition.

20 Claims, 6 Drawing Sheets

STRAP ATTACHMENT ASSEMBLY FOR AN ORTHOPEDIC BRACE

TECHNICAL FIELD

The present invention relates generally to orthopedic braces, and more particularly to a strap attachment assembly which enables a user to selectively attach or detach a strap to or from an orthopedic brace.

BACKGROUND OF THE INVENTION

Conventional orthopedic braces embody a broad range of structures, each having the common purpose of supporting and stabilizing a joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened by injury or other infirmity, thereby reinforcing the joint and reducing the risk of further injury to the joint.

Orthopedic braces may be characterized as either soft or rigid. Soft orthopedic braces are composed essentially in their entirety of soft components, i.e., relatively flexible components, such as cloth and flexible foams. An exemplary conventional soft orthopedic brace is a knee brace comprising a support sleeve formed from a stretchable elastic cloth-covered neoprene and one or more flexible, yet relatively non-stretchable, cloth straps partially or fully encircling the support sleeve. The straps may be tightened or loosened by shortening or lengthening the straps, respectively, which enables the user to adjust the fit of the brace to the knee joint and correspondingly to adjust the degree of support the brace provides the knee joint when the support sleeve is positioned over the knee joint.

In contrast to soft orthopedic braces, rigid orthopedic braces include relatively rigid structural components in addition to, or to the exclusion of, soft components. Typically, the rigid structural components of a conventional rigid orthopedic brace are support components dynamically linked together by one or more rotatable hinges enabling controlled pivotal movement of a joint on the body of a user during rehabilitative therapy or user activity. The rigid orthopedic brace is positioned on the body such that the hinges traverse the joint being stabilized, while the rigid components are secured to the body above and below the joint by a plurality of flexible straps which in combination with the rigid components encircle the body.

Figure 1:
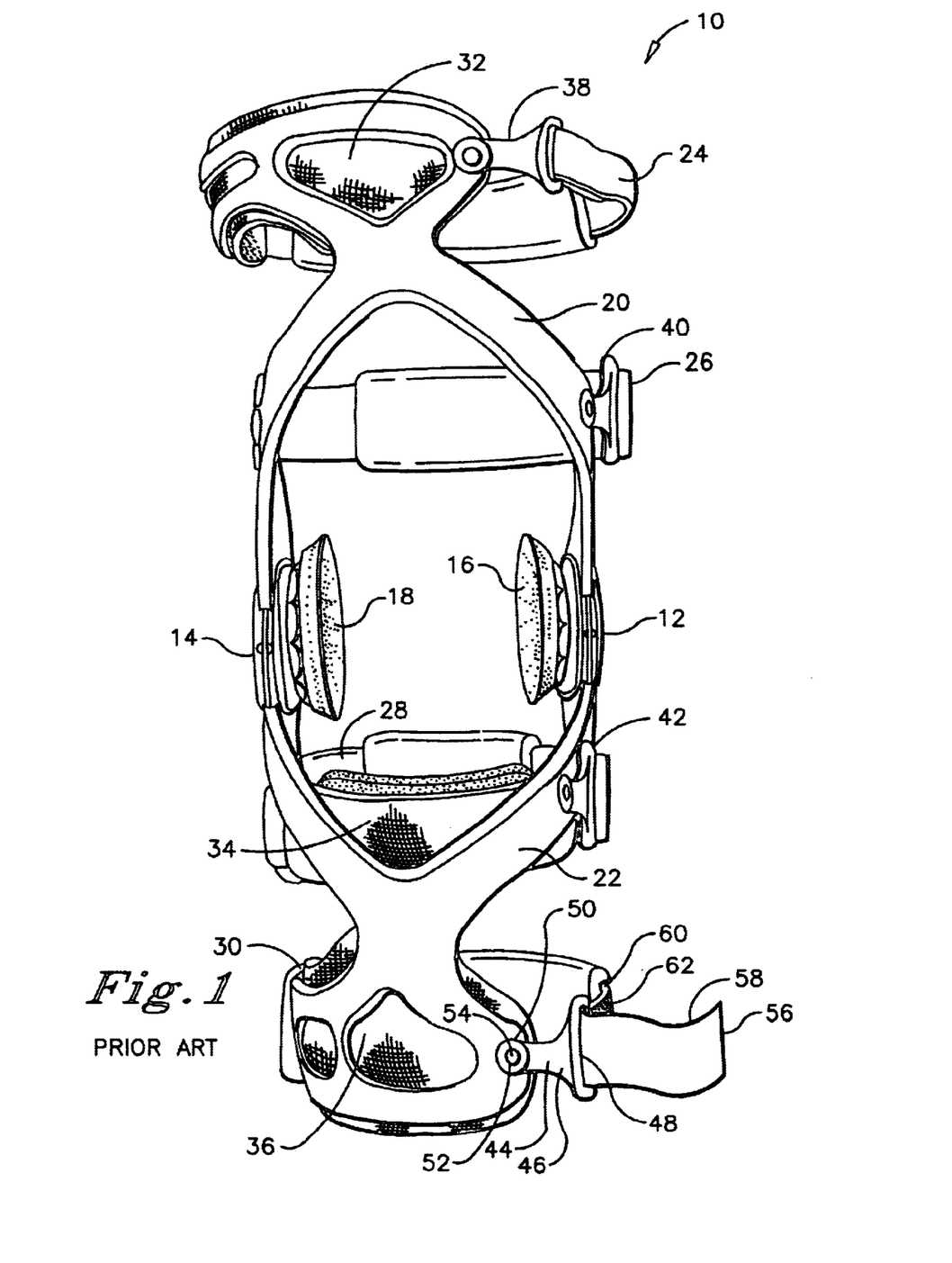
FIG. 1 is a perspective view of a prior art rigid orthopedic knee brace.

Referring to FIG. 1, an exemplary prior art rigid orthopedic brace for the knee is shown and generally designated 10. For purposes of illustration, the knee brace 10 is configured for mounting on the right leg. The knee brace 10 comprises medial and lateral hinges 12, 14 and associated medial and lateral condyle pads 16, 18. The medial and lateral hinges 12, 14 pivotally link a pair of rigid upper and lower anterior support cuffs 20, 22 which are shaped to conform to the anterior contours of the upper and lower leg, respectively. The upper anterior cuff 20 is secured in engagement with the upper leg by first and second upper straps 24, 26 which encircle the posterior of the upper leg, while the lower anterior cuff 22 is secured in engagement with the lower leg by first and second lower straps 28, 30 which encircle the posterior of the lower leg. The straps 24, 26, 28, 30 are constructed from a flexible, non-stretchable cloth, such as nylon. Anterior pads 32, 34, 36 are provided to cushion the user's leg from the rigid cuffs 20, 22 and to insure the fit of the knee brace 10 with the leg. The upper anterior pad 32 and lower anterior pads 34, 36 are attached to the upper and lower cuffs 20, 22, respectively, by conventional releasable hook and loop fasteners (not shown), which are commercially available under the trade name "VELCRO".

The cuffs 20, 22 are provided with anterior medial strap retainers 38, 40, 42, 44 which enable connection of the straps 24, 26, 28, 30 to the anterior medial side of the cuffs 20, 22. Although not visible in the view of FIG. 1, it is apparent that anterior lateral strap retainers corresponding to the anterior medial strap connectors 38, 40, 42, 44, respectively, may also be provided, which enable connection of the straps 24, 26, 28, 30 to the anterior lateral side of the cuffs 20, 22. All the strap retainers are substantially identical to one another in construction and function. Accordingly, the following description of the strap retainer 44 applies equally to the remaining strap retainers. The strap retainer 44 is constructed from a material, such as a plastic, which is non-stretchable and substantially more flexible than the rigid cuffs 20, 22, yet substantially more rigid than the flexible straps 24, 26, 28, 30. The configuration of the strap retainer 44 includes a strap loop member 46 having a strap aperture 48 extending through the strap loop member 46, and a body 50 having a mounting aperture 52 extending through the body 50. The strap retainer 44 is substantially permanently rotatably affixed to the lower cuff 22 by a fixed rivet 54 which extends through the mounting aperture 52 and a corresponding opening (not shown) in the lower cuff 22.

The strap 30 has an end 56, which is fitted with a first releasable fastener 58 on one side of the strap 30. The strap 30 correspondingly has a section 60 positioned adjacent to the end 56, which is fitted with a cooperative second releasable fastener 62 on the same side of the strap 30 as the first fastener 58. The first and second fasteners 58, 62 are preferably conventional hook and loop fasteners ("VELCRO"). The strap 30 is connected to the lower cuff 22 by means of the strap retainer 44 and the first and second fasteners 58, 62. In particular, the strap 30 is connected to the lower cuff 22 by threading the end 56 through the strap aperture 48 of the strap loop member 46 and doubling the end 56 back over the section 60 to a point on the section 60 with the first fastener 58 facing the second fastener 62. The first and second fasteners 58, 62 are then pressed against one another to releasably fasten them together. It is apparent that the user is able to adjust the strap 30, specifically, the strap length and strap tension, by selection of the point on the section 60 where the end 56 intersects the section 60.

The strap 30 is disconnected from the lower cuff 22 simply by reversing the above-recited steps for connecting the strap 30 to the lower cuff 22. In particular, the first and second fasteners 58, 62 are separated to release them from one another. The free end 56 is then backed away from the section 60 and out of the strap aperture 48.

Although the above-described prior art structure provides a reliable connection between the flexible straps and rigid cuffs of an orthopedic brace, the structure does not enable the user to releasably attach the flexible strap to the rigid cuff at a fixed point on the strap. Nor does the prior art structure enable the user to attach the flexible strap to the rigid cuff at an intermediate point on the strap, rather than an endpoint, which is often desirable. As such, the present invention recognizes a need for a means of attaching the strap to the cuff of a knee brace at a fixed point on the strap, including an intermediate point. More generally, the present invention recognizes a need for a means of releasably attaching a strap to another component of an orthopedic brace at a fixed point on the strap, including an intermediate point.

Accordingly, it is an object of the present invention to provide a strap attachment assembly which enables releasable attachment or detachment of a strap to or from another component of an orthopedic brace. More particularly, it is an object of the present invention to provide a strap attachment assembly which enables releasable attachment or detachment of the strap to or from the posterior side of the orthopedic brace. It is a further object of the present invention to provide such a strap attachment assembly having a strap retainer which engages the strap at a fixed point on the strap. It is still a further object of the present invention to provide such a strap attachment assembly having a strap retainer which engages the strap at a fixed intermediate point on the strap. It is yet another object of the present invention to provide a strap attachment assembly which maintains releasable attachment of the strap to the orthopedic brace regardless of the direction in which the strap attachment assembly or strap is stressed during normal use. These objects and others are accomplished in accordance with the invention described hereafter. Elements of the present invention have also been described in my copending U.S. patent application filed on Mar. 14, 2002, entitled "Strap Connector Assembly for an Orthopedic Brace", incorporated herein by reference.

SUMMARY OF THE INVENTION

The present invention is a strap attachment assembly for an orthopedic brace comprising an anchor, preferably mounted on an orthopedic brace component, and a strap retainer, preferably mounted on a strap. The anchor includes a retention post and a retention head mounted on the retention post. The retention head has an outer boundary defining a diameter substantially greater than a corresponding diameter of the retention post. The strap retainer has a body and a retention plate. The body includes a chamber having a diameter less than the diameter of the retention head and greater than or equal to the diameter of the retention post. The retention plate includes a retention opening formed in a surface of the retention plate. The retention opening is aligned with the chamber. The retention opening has an inner boundary defining a diameter greater than or equal to the diameter of the retention head to releasably receive the retention head in the retention opening when the retention post is positioned in the chamber. The retention plate is transitionable between a locked condition and an unlocked condition. The inner boundary of the retention opening is positioned adjacent to the outer boundary of the retention head to block displacement of the outer boundary in a direction past the inner boundary in the locked condition. The inner boundary is positioned clear of the outer boundary to permit displacement of the outer boundary in the direction past the inner boundary in the unlocked condition.

In accordance with another embodiment, the present invention is a strap attachment assembly for an orthopedic brace comprising an anchor, preferably mounted on an orthopedic brace component, and a strap retainer, preferably mounted on a strap. The anchor includes a retention head having an outer boundary defining a diameter. The strap retainer includes a retention plate transitionable between a locked condition and an unlocked condition. The retention plate has a retention opening formed in its surface. The retention opening has an inner boundary defining a diameter greater than or equal to the diameter of the retention head to retain the retention head in the retention opening when the retention plate is in the locked condition by positioning the inner boundary adjacent to the outer boundary of the retention head and blocking displacement of the outer boundary in a direction past the inner boundary. Conversely, the retention opening releases the retention head when the retention plate is in the unlocked condition by positioning the inner boundary clear of the outer boundary and permitting displacement of the outer boundary in the direction past the inner boundary. The strap attachment assembly further comprises means for biasing the retention plate in the locked condition.

The present invention is also a method for attaching a strap to an orthopedic brace. The method provides an anchor mounted on the orthopedic brace component. The anchor includes a retention head having an outer boundary defining a diameter. The method further provides a strap retainer mounted on a strap. The strap retainer has a retention plate including a retention opening. The retention opening has an inner boundary defining a diameter greater than or equal to the diameter of the retention head. The method enables selective transitioning of the retention plate between a locked condition and an unlocked condition, wherein the retention plate is biased in the locked condition. The locked condition is effected by positioning the outer boundary of the retention head adjacent to the inner boundary of the retention opening to block displacement of the outer boundary in a direction past the inner boundary. The unlocked condition is effected by positioning the outer boundary clear of the inner boundary to permit displacement of the outer boundary in a direction past the inner boundary. The present invention will be further understood from the drawings and the following detailed description.

DESCRIPTION OF PREFERRED EMBODIMENTS

Figure 2:
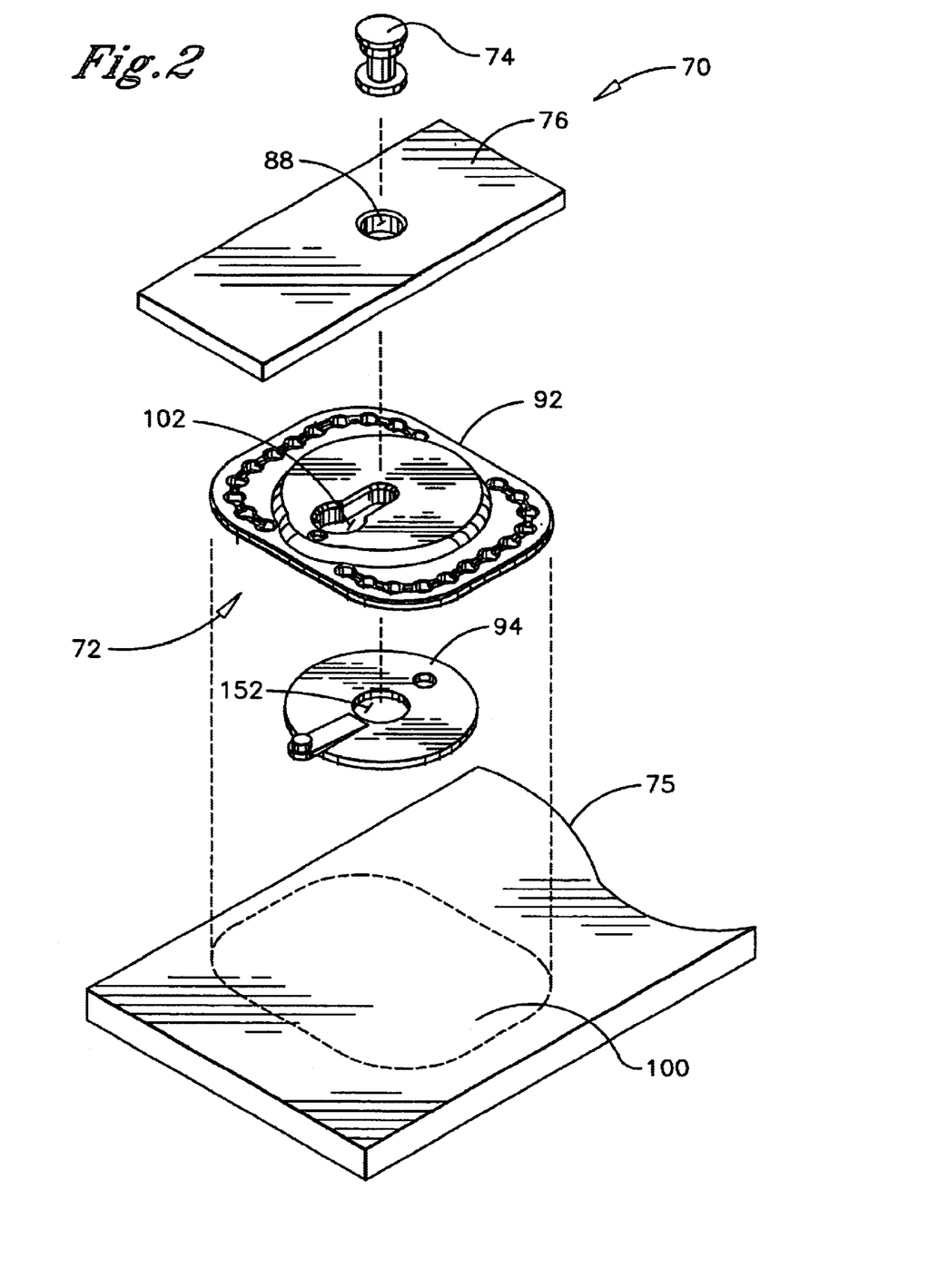
FIG. 2 is an exploded perspective view of a strap attachment assembly of the present invention, which includes a strap retainer and anchor, shown in association with a strap and an orthopedic brace component.

Referring to FIG. 2, a strap attachment assembly of the present invention is shown and generally designated 70. The strap attachment assembly 70 comprises in combination a strap retainer 72 and an anchor 74. The strap retainer 72 and anchor 74 are cooperatively configured to enable connection of the strap retainer 72 to the anchor 74 and correspondingly attachment of a strap 75 to an orthopedic brace component 76 in a manner described hereafter. The strap 75 and orthopedic brace component 76 are shown only partially herein. The strap retainer 72 and anchor 74 are additionally cooperatively configured to enable disconnection of the strap retainer 72 from the anchor 74 and correspondingly detachment of the strap 75 from the orthopedic brace component 76.

The strap 75 is any conventional strap which is typically constructed from either a natural or synthetic cloth, such as nylon, rayon, or the like. The strap 75 is preferably relatively flexible, yet relatively non-stretchable. The orthopedic brace component 76 may be any one of the multiple components of a conventional orthopedic brace and is preferably a support member or a hinge. For example, the orthopedic brace component 76 may be the rigid support cuff of a rigid knee brace, as shown in FIG. 1.

Figure 3:
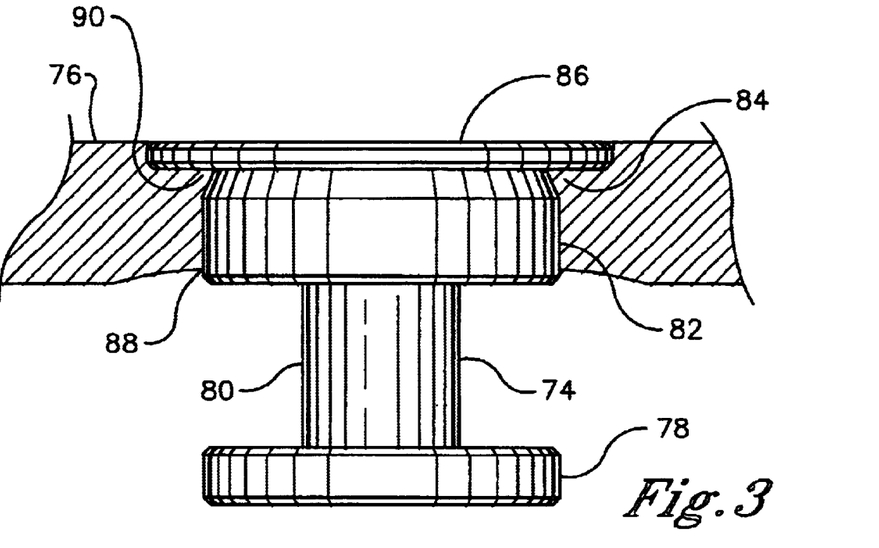
FIG. 3 is a cross-sectional plan view of the anchor of FIG. 2 fixably mounted on the orthopedic brace component.

Referring additionally to FIG. 3, the anchor 74 is a rigid member fixably mountable on the orthopedic brace component 76. The anchor 74 is preferably fabricated as an integral form from a high-strength material such as steel. The anchor 74 is configured in a series of dimensionally distinct sections, which include, from bottom to top, a retention head 78, a retention post 80, a mounting post 82, a mounting notch 84, and a mounting base 86. The retention head 78, retention post 80, mounting post 82, and mounting notch 84 are all sized to fit through a continuous anchor opening 88 extending through the entire thickness of the orthopedic brace component 76. As such, the retention head 78 and retention post 80 each has a diameter substantially less than that of the anchor opening 88. The mounting post 82 has a diameter essentially equal to the diameter of the anchor opening 88 and the mounting base 86 has a diameter substantially greater than that of the anchor opening 88. It is further noted that the retention head 78 has a diameter substantially greater than that of the retention post 80 and less than or equal to that of the mounting post 82.

The anchor 74 is fixably mounted to the orthopedic brace component 76 by press fitting the anchor 74 though the top of the anchor opening 88 until the mounting post 82 and mounting base 86 are essentially flush with the bottom and top of the anchor opening 88, respectively. Specifically, the retention head 78 and retention post 80 are displaced downwardly through the anchor opening 88 so that the mounting post 82 engages the sidewall of the anchor opening 88. The mounting post 82 is pressed downwardly into the anchor opening 88 so that the mounting base 86 engages the top edge 90 of the anchor opening 88. The mounting base 86 is then pressed downwardly into the anchor opening 88 with sufficient force to deform and displace the top edge 90 of the anchor opening 88 into the mounting notch 84, which fixably retains the anchor 74 in the anchor opening 88 thereafter.

It is understood that other alternate configurations of the anchor and techniques for mounting the anchor on the orthopedic brace component not shown or described in detail herein are possible within the scope of the present invention. For example, the anchor can be mounted on the orthopedic brace component by alternate techniques such as threading, crimping, bonding, welding, fastening, sewing or other techniques known to the skilled artisan. Alternate configurations of the anchor suitable for practice of the present invention provide a retention post 80 and alternate means within the purview of the skilled artisan for mounting the retention post on the orthopedic brace component other than the above-described mounting aperture 52, mounting post 82, mounting notch 84 and mounting base 86. Alternate configurations of the anchor also preferably (but optionally) provide a retention head 78. The optional retention head 78, retention post 80 and orthopedic brace component 76 are oriented to one another as shown in FIG. 3 such that the plane of the retention head 78 extends below the plane of the orthopedic brace component 76 a distance, which essentially corresponds to the length of the retention post 80. In addition, the longitudinal axis of the retention post 80 is oriented essentially perpendicular to the plane of the retention head 78 and the plane of the orthopedic brace component 76.

Referring to FIG. 2, the strap retainer 72 comprises a body 92 and a retention plate 94, which resides substantially within the body 92 when unstressed. Both the body 92 and the retention plate 94 are preferably constructed from a high-strength material, such as a plastic, by means such as conventional molding. The material of the strap retainer 72 and the resulting strap retainer 72 itself are typically more flexible than the material of the anchor 74 and the anchor 74 itself, while substantially more rigid than the material of the strap 75 and the strap itself 75. The body 92 has a three-dimensional configuration. However, the magnitude of the length and width is substantially greater than the magnitude of the height, which affords the body 92 a low profile.

Figure 4:
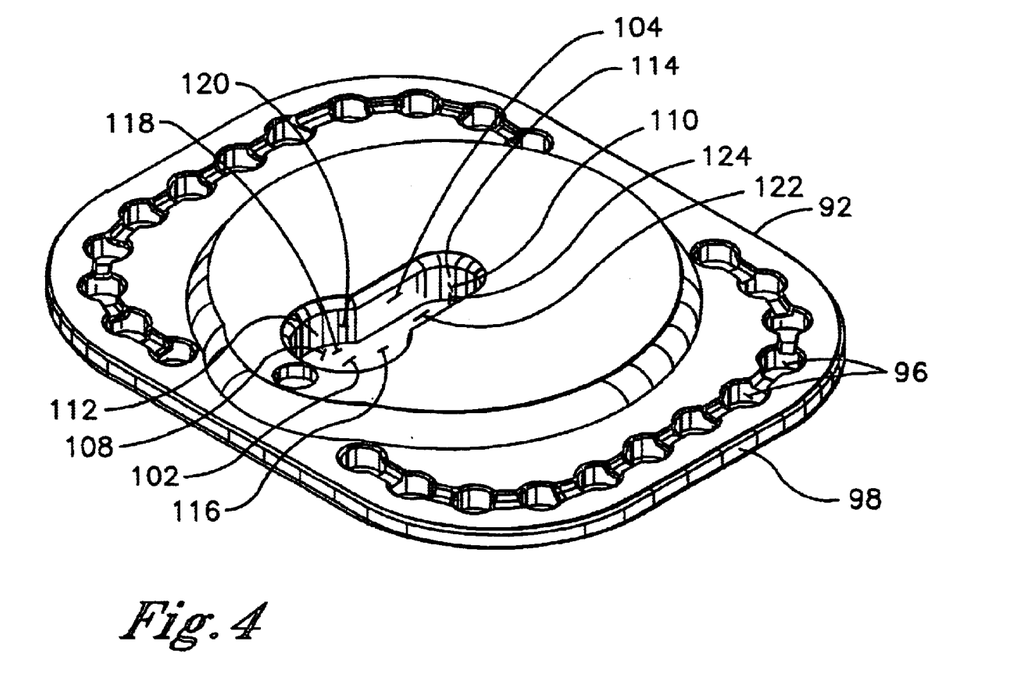
FIG. 4 is a top perspective view of the body of the strap retainer of FIG. 2.
Figure 5:
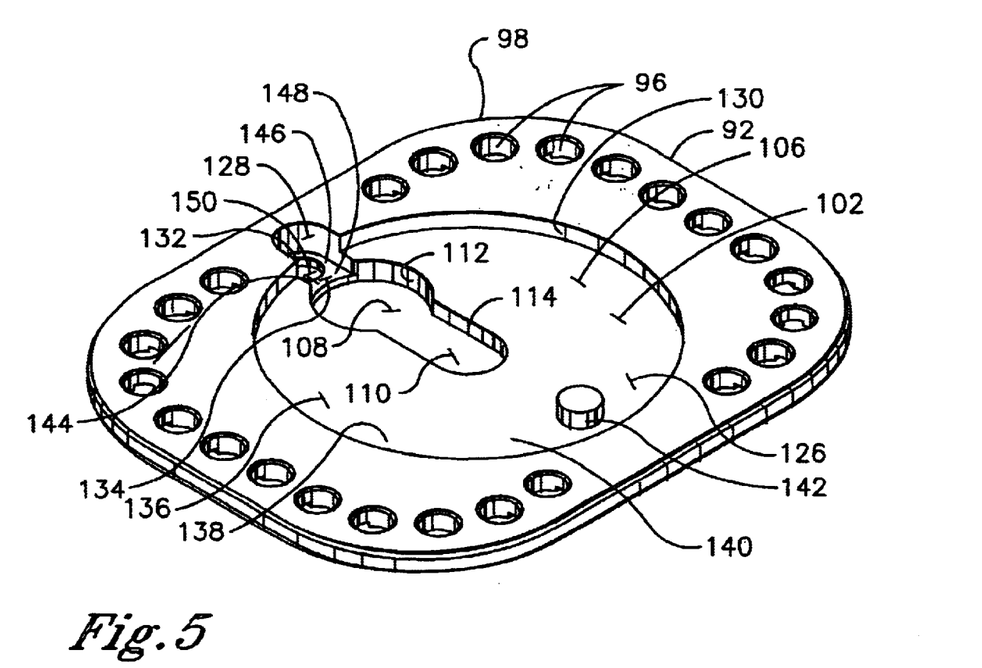
FIG. 5 is a bottom perspective view of the body of the strap retainer of FIG. 2.

Referring additionally to FIGS. 4 and 5, a plurality of eyelets 96 are serially formed in the body 92 proximal to the perimeter 98, with each eyelet 96 extending through the entire thickness of the body 92. The eyelets 96, in association with sewing thread (not shown), are a preferred means of providing essentially permanent attachment of the body 92 to the strap 75 at a fixed location 100 on the strap 75, which may be an endpoint or an intermediate point on the strap 75. The term "permanent attachment" as used herein refers to an attachment which is irreversible, i.e., the attachment cannot be easily released without destroying at least some portion of the attachment means. It is further apparent to the skilled artisan that there are many other known means of permanently attaching a relatively rigid member to cloth which fall within the scope of the present invention, such as bonding with glue or other adhesives, or fastening with staples, rivets, pins or other fasteners.

The body 92 has a void 102 extending through the thickness of the body 92. The void 102 has a large volume relative to each eyelet 96 and is generally positioned interior to the eyelets 96 on the body 92. The void 98 is segmented, both vertically and horizontally, into a plurality of interconnected chambers. It is noted that the terms "vertical" and "horizontal", as well as the terms "upper" and "lower", are used herein to denote the spatial orientation of the elements of the strap attachment assembly 70 relative to one another as displayed in FIG. 2. The terms do not necessarily reflect the spatial orientation of the elements in absolute terms with respect to the external environment when the strap attachment assembly 70 is in a preferred operational orientation.

The void 98 is vertically segmented into an upper chamber 104 and a lower chamber 106, wherein the lower chamber 106 is positioned directly beneath the upper chamber 104. The upper chamber 104 is horizontally segmented into a first upper chamber 108 and a second upper chamber 110, which are positioned horizontally adjacent to one another. The first upper chamber 108 has a first upper inner surface 112 which defines in part a concave side boundary of the first upper chamber 108. Although not continuous, the path of the first upper inner surface 112 forms a partial circle. The second upper chamber 110 has a second upper inner surface 114 which similarly defines in part a concave side boundary of the second upper chamber 110. Although not continuous, the path of the second upper inner surface 114 forms a partial oval. The second upper chamber 110 has a diameter substantially less than that of the first upper chamber 108, wherein the diameter of a non-circular shape is defined herein as the diameter of the smallest circle enclosing (or the largest circle fitting) within the non-circular shape.

The first and second upper chambers 108, 110 horizontally intersect at a shared upper opening 116 which results from discontinuities in both the first and second upper inner surfaces 112, 114. As such, the shared upper opening 116 defines a transition interface and an open horizontal pathway between the first and second upper chambers 108, 110. The first upper chamber 108 is vertically open at first and second opposing faces 118, 120 of the first upper chamber 108. The second upper chamber 110 is similarly vertically open at first and second opposing faces 122, 124 of the second upper chamber 110. The open first opposing faces 118, 122 enable direct communication between the external environment and the first and second upper chambers 108, 110, respectively. The open second opposing faces 120, 124 enable direct communication between the lower chamber 106 and the first and second upper chambers 108, 110, respectively.

The lower chamber 106 is horizontally segmented into a first lower chamber 126 and a second lower chamber 128, which are positioned horizontally adjacent to one another. The first lower chamber 126 has a first lower inner surface 130 which defines in part a concave side boundary of the first lower chamber 108. Although not continuous, the path of the first lower inner surface 130 forms a partial circle. The second lower chamber 128 has a second lower inner surface 132 which similarly defines in part a concave side boundary of the second lower chamber 128. Although not continuous, the path of the second lower inner surface 132 forms a partial oval. The first lower chamber 126 has a diameter substantially greater than that of either the second lower chamber 128, the first upper chamber 108, or the second upper chamber 110. The first and second lower chambers 126, 128 horizontally intersect at a shared lower opening 134 which results from discontinuities in both the first and second lower inner surfaces 130, 132. As such, the shared lower opening 134 defines an open horizontal pathway between the first and second lower chambers 126, 128.

The first lower chamber 126 has first and second opposing faces 136, 138 and is vertically open at the first opposing face 136, but is partially covered by a discontinuous first cover surface 140 at the second opposing face 138. The discontinuities in the first cover surface 140 correspond identically to the open first opposing faces 120, 124 of the first and second upper chambers 106, 108, respectively, thereby providing open vertical pathways between the first lower chamber 126 and the first and second upper chambers 106, 108, respectively. A cylindrically shaped alignment pin 142 extends downwardly from the relatively smooth and flat first cover surface 140 substantially at a right angle to the first cover surface 140 and from a position on the first cover surface 140 substantially opposite the first opposing face 118.

The second lower chamber 128 similarly has first and second opposing faces 144, 146 and is vertically open at the first opposing face 144, but is partially covered by a discontinuous second cover surface 148 at the second opposing face 146. The discontinuity in the second cover surface 148 is a release pin aperture 150 extending through the entire thickness of the second cover surface 148. The release pin aperture 150 has a diameter essentially comparable to that of each of the eyelets 96 and substantially less than that of the chambers; 108, 110, 126, 128. The release pin aperture 150 provides an open vertical pathway between the second lower chamber 128 and the external environment. It is noted that the second lower chamber 128 has a height somewhat greater than that of the first lower chamber 126, because the second cover surface 148 is elevated relative to the first cover surface 140.

Figure 6:
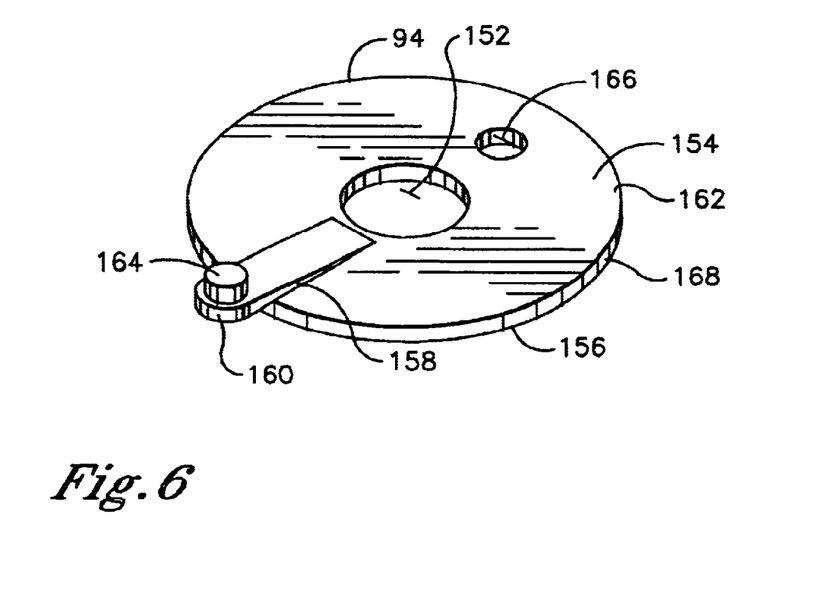
FIG. 6 is a top perspective view of the retention plate of the strap retainer of FIG. 2.

Referring additionally to FIG. 6, the retention plate 94 has an annular configuration with a centrally positioned retention opening 152 extending through the entire thickness of the retention plate 94. The retention plate 94 has first and second opposite surfaces 154, 156, which are relatively smooth and flat. However, the first opposite surface 154 has a wedge-shaped ramp 158 upwardly extending therefrom. The ramp 158 has a radially ascending gradient extending outwardly from the retention opening 138. An extended portion 160 of the ramp 158 advances radially past the side boundary at the perimeter 162 of the retention plate 94. The second lower chamber 128 is sized to receive the extended portion 160 therein. As such the extended portion 160 has a width less than or equal to the diameter of the second lower chamber 128 and an apex less than or equal to the height of the second lower chamber 128.

A release pin 164 is positioned on the extended portion 160 at or near the apex of the ramp 158. The release pin 164 has a substantially perpendicular orientation to the first opposite surface 154 and is oriented and sized to be slidably received within the release pin aperture 150 of the second cover surface 148. As such the release pin 164 has a diameter less than or equal to that of the release pin aperture 150. An alignment pin aperture 166 is positioned in the retention plate 94 radially opposite the ramp 158 and release pin 164. The alignment pin aperture 166 extends through the entire thickness of the retention plate 94 and is oriented and sized to slidably receive the alignment pin 142 of the first cover surface 140. As such, the alignment pin aperture 166 has a diameter greater than or equal to that of the alignment pin 142.

The bulk of the retention plate 94 is sized to fit substantially within the first lower chamber 126 although, as noted above, the extended portion 160 of the ramp 158 and release pin 164 are sized to fit within the second lower chamber 128 and retention pin aperture 150, respectively. Accordingly, excluding the ramp 158 and release pin 164, the retention plate 94 has a thickness substantially less than that of the body 92, preferably ranging from slightly greater than the height of the first lower chamber 126 to somewhat less than the height of the first lower chamber 126. The retention plate 94 has a continuous outer sidewall 168 which defines a convex side boundary of the retention plate 94 and forms a complete circle. The outer sidewall 168 has a diameter less than or equal to that of the first lower chamber 126 enabling the retention plate 94 to be seated in the first lower chamber 126. When the retention plate 94 is seated in the first lower chamber 126, the retention opening 152 is vertically aligned with the second upper chamber 110 directly thereunder. In addition, the outer sidewall 168 of the retention plate 94 is proximal to or in engagement with the first lower inner surface 130.

The relative dimensions of the anchor 74, body 92, and retention plate 94 enable the desired function of the strap attachment assembly 70. In particular, the diameter of the retention head 78 is substantially less than the diameter of the first lower chamber 126, less than or equal to the diameter of the first upper chamber 108 and greater than the diameter of the second upper chamber 110. The diameter of the retention head 78 is also less than or equal to the diameter of the retention opening 152. The diameter of the second upper chamber 110 is equal to or greater than the diameter of the retention post 80. The length of the retention post 80 is greater than or equal to the height of the second upper inner surface 114.

Method of Operation

Operation of the strap attachment assembly 70, wherein the strap retainer 72 is attached to the anchor 74 (and correspondingly the strap 75 is attached to the orthopedic brace component 76), is described hereafter with reference to FIGS. 7–10. Each one of FIGS. 7–10 shows a different position of the strap attachment assembly 70 at a specific point in time, while performing a sequence of steps for attachment of the strap 75 to the orthopedic brace component 76.

Figure 7:
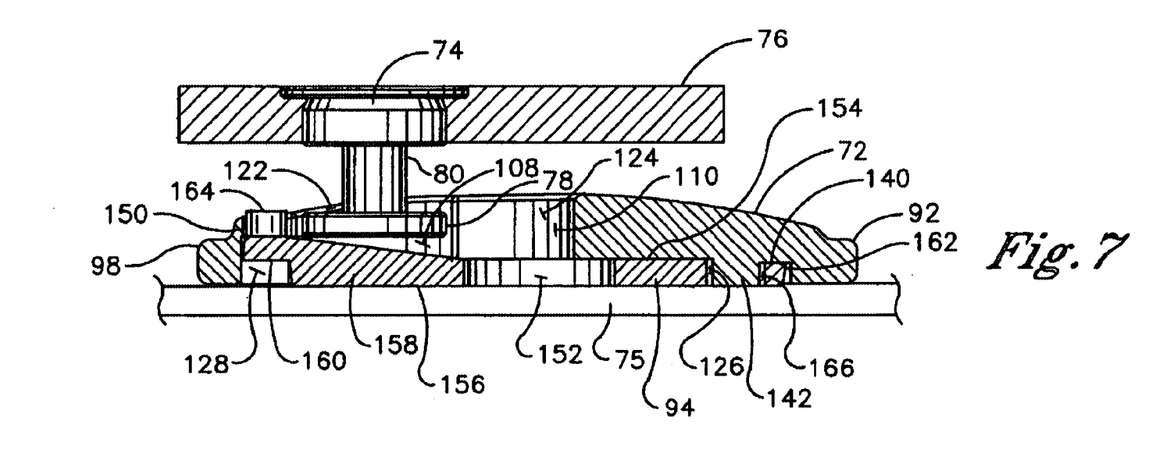
FIG. 7 is a cross-sectional plan view of the strap attachment assembly of FIG. 2 after a first attachment step.
Figure 8:
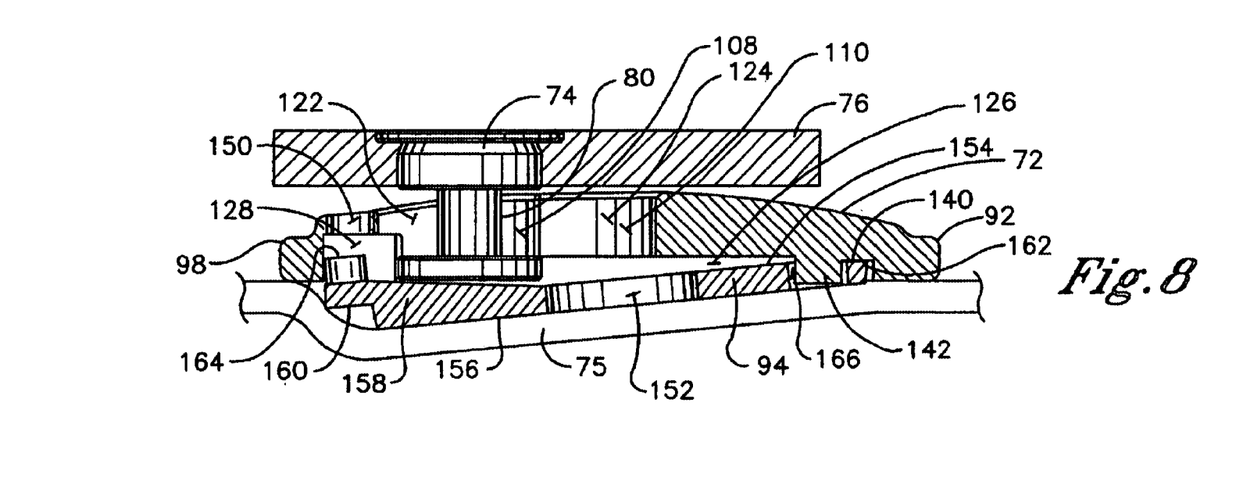
FIG. 8 is a cross-sectional plan view of the strap attachment assembly of FIG. 2 after a second attachment step.

Referring initially to FIG. 7, the strap attachment assembly 70 is shown upon completion of a first attachment step, wherein the body 92 has been manually displaced upwardly into engagement with the anchor 74. The retention head 78 is positioned in the first upper chamber 108 directly above the ramp 158 residing in the first and second lower chambers 126, 128. Referring to FIG. 8, the strap attachment assembly 70 is shown upon completion of a second attachment step, wherein upward manual displacement of the body 92 has continued. The retention head 78 has passed upwardly through the first upper chamber 108 and is positioned in the first lower chamber 126, while the retention post 80 is positioned in the first upper chamber 108. The bottom of the retention head 78 has engaged the ramp 158 in the first lower chamber 126.

The upward displacement force of the body 92 has caused the retention head 78 to apply a counter force which stresses the retention plate 94. In particular, the side of the retention plate 94, on which the ramp 158 is mounted, is subjected to a downward counter force by the retention head 78, which rotationally displaces the ramp 158 downwardly away from the body 92. The opposite side of the retention plate 94, where the alignment pin aperture 166 is positioned, is blocked from corresponding upward rotational displacement by retention of the alignment pin 142 in the alignment pin aperture 166 and abutment of the perimeter 162 of the retention plate 94 against the first cover surface 140. Thus, the retention plate 94 pivots about the point where the alignment pin 142 and perimeter 162 engage the alignment pin aperture 166 and first cover surface 140, respectively, in response to being stressed by the retention head 78. Pivoting the retention plate 94 elastically deflects the ramp 158 away from the body 92 until there is sufficient clearance between the first opposite surface 154 and the second upper inner surface 114 to enable the entire thickness of the retention head 78 to slide horizontally under the second upper inner surface 114.

It is noted that deflection of the ramp 158 is elastic because there is a continuous upward biasing force exerted on the second opposite surface 156 of the retention plate 94 throughout operation of the strap attachment assembly 70. Although the upward biasing force on the retention plate 94 is generally less than the pivoting force downwardly displacing the ramp 158 away from the body 92 during the second attachment step, the biasing force nevertheless applies a resistance to the pivoting force. The biasing force results from a number of contributors. For example, the cloth strap 75 engaging the second opposite surface 156 on the back of the retention plate 94 has a nap which exerts a continuous upward force against the retention plate 94. In addition, when the orthopedic brace component 76 is mounted on a user (not shown), the strap attachment assembly 70 is preferably positioned on the posterior side of the orthopedic brace component 76, i.e., the side facing the user, with the anchor 74 mounted on the orthopedic brace component 76. As such, the elastic skin of the user exerts an upward force against the second opposite surface 156 of the retention plate 94. The material of the retention plate 94 also has a degree of elasticity which contributes to the biasing force when the retention plate 94 is pivoted. Other means not shown for applying an upward biasing force to the retention plate 94 when the retention plate 94 is deflected or otherwise stressed, such as an elastic hinge, a leaf spring or the like, are readily within the purview of the skilled artisan and fall within the scope of the present invention.

Figure 9:
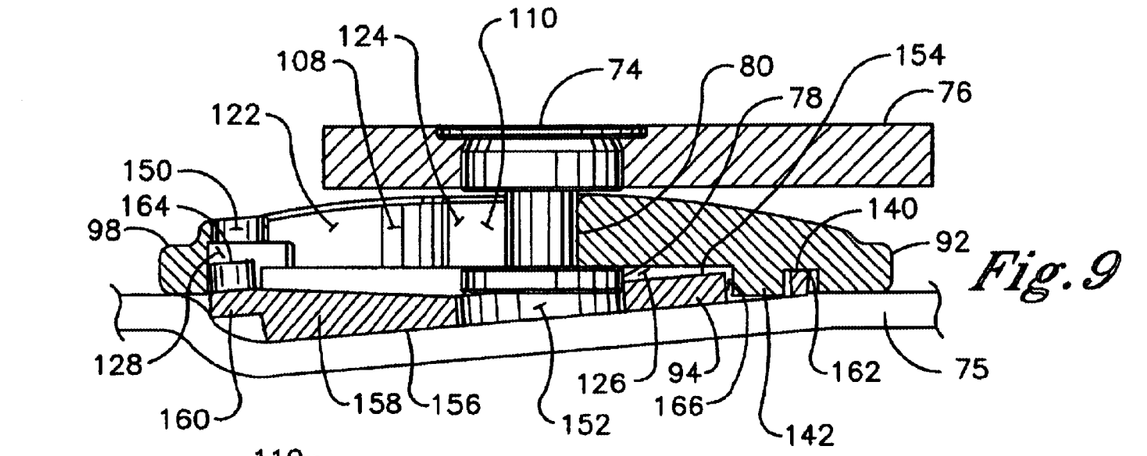
FIG. 9 is a cross-sectional plan view of the strap attachment assembly of FIG. 2 after a third attachment step.

Referring to FIG. 9, the strap attachment assembly 70 is shown upon completion of a third attachment step, wherein the retention head 78 has been slidably displaced along the surface of the ramp 153 away from the ramp 158 toward the retention opening 152. In doing so, the retention head 78 has deflected the ramp 158 downward a sufficient deflection distance, which has enabled the retention head 78 to pass beneath the second upper inner surface 114 into vertical alignment with the retention opening 152. The retention post 80 is simultaneously positioned in the second upper chamber 110, which positions the retention head 78 in engagement or near engagement with the first cover surface 140, thereby preventing upward vertical displacement of the anchor 74 from the body 92. It is noted that the ramp 158, as shown in FIG. 9, is in a stressed or deflected position for purposes of illustration only. In practice, the upward biasing force on the retention 94 would urge the retention plate 94 back into an unstressed or undeflected position within the void 102 substantially instantaneously upon alignment of the retention head 78 with the retention opening 152.

Figure 10:
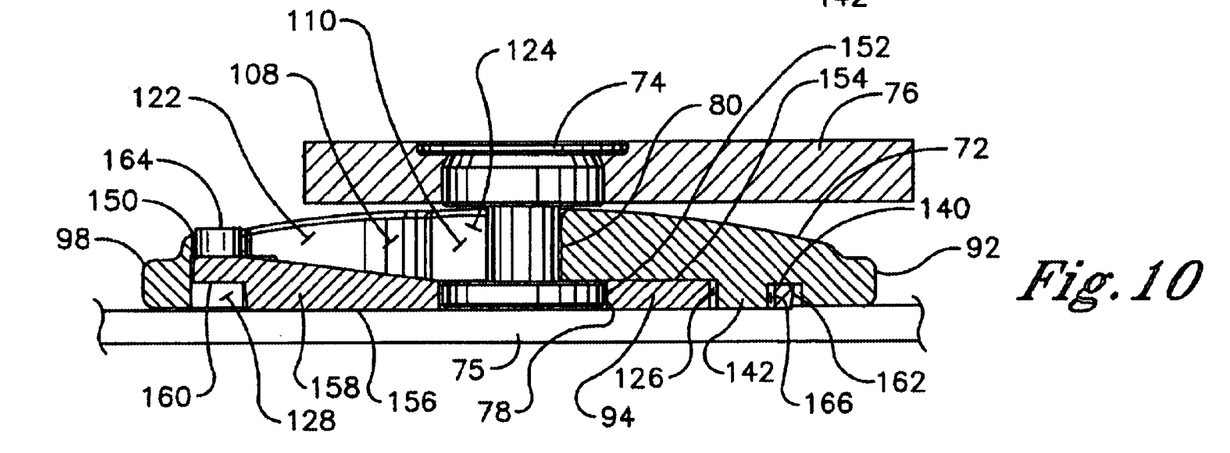
FIG. 10 is a cross-sectional plan view of the strap attachment assembly of FIG. 2 after a fourth attachment step.

Referring to FIG. 10, the strap attachment assembly 70 is shown upon completion of a fourth attachment step, wherein the strap attachment assembly 70 has transitioned to a locked condition, thereby essentially completing the operation of attaching the strap 75 to the orthopedic brace component 76. The locked condition is so termed because the anchor 74 is essentially "locked" into engagement with the strap retainer 72. Once in the locked condition, the anchor 74 cannot be readily detached from the strap retainer 72 without applying a relatively substantial manual downward displacement force to the retention plate 94. In particular, the displacement force must be sufficient to overcome the upward biasing force on the retention plate 94 which resists downward deflection of the ramp 158.

When the strap attachment assembly 70 is in the locked condition, the anchor 74 no longer exerts a downward counter force on the retention plate 94 which exceeds the upward biasing force. Accordingly, the upward biasing force has returned the retention plate 94 to the unstressed or undeflected position, wherein the retention head 78 has been received and resides within the retention opening 152, the extended portion 160 of the ramp 158 has been received and resides within the second lower chamber 128, and the release pin 164 has been received and resides within the release pin aperture 166. The bulk of the retention plate 94 is retained within the first lower chamber 126 and is essentially flush or at least nearly flush with the second opposite surface 156 of the retention plate 94.

The unstressed or undeflected retention plate 94 prevents unintended detachment of the anchor 74 and strap retainer 72 irrespective of the direction of the forces applied to the strap attachment assembly 70 by the strap 75 or orthopedic brace component 76. In particular, the inner boundary of the retention opening 152 is maintained adjacent to the outer boundary of the retention head 78 by the upward biasing force. The spatial relation of the retention opening 152 and retention head 78 effectively prevents horizontal movement of the retention head 78 away from vertical alignment with the second upper chamber 110 into vertical alignment with the first upper chamber 108. If the retention head 78 was otherwise permitted to move into vertical alignment with the first upper chamber 108, the open second opposing face 120 would enable vertical withdrawal of the anchor 74 from the strap retainer 72 via the first upper chamber 108.

It is apparent from the above that the anchor 74 is detached from the strap retainer 72 (and correspondingly the strap 75 is detached from the orthopedic brace component 76) by reversing the above-recited operational steps of attaching the strap 75 to the orthopedic brace component 76. To initiate detachment, the strap attachment assembly 70 is transitioned to the unlocked position. Specifically, the ramp 158 is manually displaced downward so that the inner boundary of the retention opening 152 is correspondingly deflected downward to clear away from the outer boundary of the retention head 78 as shown in FIG. 9, thereby enabling horizontal displacement of the retention head 78 away from the retention opening 152. Manual downward displacement of the ramp 158 is preferably performed by inserting a pointed object, such as a ball point pen tip, a pin or a paper clip end, into the release pin aperture 150 to engage and depress the release pin 164. The retention head 78 is then horizontally displaced away from vertical alignment with the second upper chamber 110 while engaging the surface of the ramp 158 until the retention head 78 comes into vertical alignment with the first upper chamber 108. The retention post 80 simultaneously exits the second upper chamber 110 and enters the first upper chamber 108 as shown in FIG. 8. The retention head 78 is displaced through the open second opposing face 120 into the first upper chamber 108 as shown in FIG. 7. This condition enables vertical withdrawal of the anchor 74 from the body 92 with a negligible manual displacement force to effect detachment of the strap 75 from the orthopedic brace component 76.

In accordance with the present preferred embodiment of the strap attachment assembly 70, as described above, the anchor 74 is mounted, preferably posteriorly, on the orthopedic brace component 76 and the strap retainer 72 is mounted on the strap 75. It is further within the scope of the present invention to reverse the relation of the anchor and the strap retainer to the orthopedic brace component and strap, respectively. Thus the present invention further includes embodiments of the strap attachment assembly, wherein the strap retainer is mounted on the orthopedic brace component and the anchor is mounted on the strap. It is apparent that reversing the relation of the anchor and strap retainer to the orthopedic brace component and strap, respectively, to mount the strap retainer on the orthopedic brace component and mount the anchor on the strap requires some modification of the embodiment disclosed above to render the strap attachment assembly operative. However, such modifications are clearly within the purview of the skilled artisan when combined with the teachings herein. It is further understood that the tern "mounted on" as used herein is broadly inclusive and encompasses elements which are integral with one another, attached to one another, or are otherwise connected to one another either directly or indirectly. However, the term "mounted on" is not inclusive of releasable retention of the anchor 74 within the void 98 as described above.

While the forgoing preferred embodiments of the invention have been described and shown, it is understood that alternatives and modifications, such as those suggested and others, may be made thereto and fall within the scope of the invention.

Glossary of Drawing Terms Attorney Docket No. 001P0201

10 prior art orthopedic knee brace
12 medial hinge
14 lateral hinge
16 medial condyle pad
18 lateral condyle pad
20 upper anterior cuff
22 lower anterior cuff
24 first upper strap
26 second upper strap
28 first lower strap
30 second lower strap
32 upper anterior pad
34 lower anterior pad
36 lower anterior pad
38 strap retainer
40 strap retainer
42 strap retainer
44 strap retainer
46 strap loop member
48 strap aperture
50 body
52 mounting aperture
54 rivet
56 end (30)
58 first fastener
60 section (30)
62 second fastener
70 strap attachment assembly
72 strap retainer
74 anchor
75 strap
76 orthopedic brace component
78 retention head (74)
80 retention post (74)
82 mounting post (74)
84 mounting notch (74)
86 mounting base (74)
88 anchor opening (74)
90 top edge (88)
92 body
94 retention plate
96 eyelets (92)
98 perimeter (92)
100 fixed location (75)
102 void (92)
104 upper chamber (102)
106 lower chamber (102)
108 first upper chamber (104)
110 second upper chamber (104)
112 first upper inner surface (108)
114 second upper inner surface (110)
116 shared upper opening (108, 110)
118 open first opposing face (108)
120 open second opposing face (108)
122 open first opposing face (110)
124 open second opposing face (110)
126 first lower chamber (106)
128 second lower chamber (106)
130 first lower inner surface (126)

132 second lower inner surface (128)
134 shared lower opening (106)
136 open first opposing face (126)
138 second opposing face (126)
140 first cover surface (138)
142 alignment pin (140)
144 open first opposing face (128)
146 second opposing face (128)
148 second cover surface (146)
150 release pin aperture (148)
152 retention opening (94)
154 first opposite surface (94)
156 second opposite surface (94)
158 ramp (154)
160 extended portion (158)
162 perimeter (94)
164 release pin (158)
166 alignment pin aperture (94)
168 outer sidewall (94)

I claim:

1. A strap attachment assembly for an orthopedic brace comprising:
an anchor mounted on an orthopedic brace component, said anchor comprising a retention post and a retention head mounted on said retention post, wherein said retention head has an outer boundary defining a diameter substantially greater than a corresponding diameter of said retention post; and
a strap retainer mounted on a strap, said strap retainer comprising a body and a retention plate, said body including a chamber having a diameter less than said diameter of said retention head and greater than or equal to said diameter of said retention post, said retention plate including a retention opening formed in a surface of said retention plate, said retention opening aligned with said chamber and having an inner boundary defining a diameter greater than or equal to said diameter of said retention head to releasably receive said retention head in said retention opening when said retention post is positioned in said chamber, wherein said retention plate is transitionable between a locked condition and an unlocked condition, said inner boundary of said retention opening positioned adjacent to said outer boundary of said retention head to block displacement of said outer boundary in a direction past said inner boundary in said locked condition and said inner boundary positioned clear of said outer boundary to permit displacement of said outer boundary in said direction past said inner boundary in said unlocked condition.

2. The strap attachment assembly of claim 1 further comprising means for biasing said retention plate in said locked condition.

3. The strap attachment assembly of claim 2 wherein said biasing means is flexion of said retention plate.

4. The strap attachment assembly of claim 2 wherein said biasing means is said strap.

5. The strap attachment assembly of claim 1 wherein said surface of said retention plate has a raised portion adjacent to said retention opening.

6. The strap attachment assembly of claim 5 wherein said retention plate has a pivot point on said surface substantially opposite said raised portion, said pivot point pivotally engageable with said body when said raised portion is displaced away from said body.

7. The strap attachment assembly of claim 1 wherein said surface of said retention plate has a raised portion offset from said chamber.

8. The strap attachment assembly of claim 7 wherein said chamber is a first chamber and said diameter of said chamber is a first chamber diameter, said body further including a second chamber adjacent to said first chamber, said second chamber having a second chamber diameter greater than or equal to said diameter of said retention head.

9. The strap attachment assembly of claim 8 wherein said second chamber is aligned with said raised portion.

10. The strap attachment assembly of claim 1 wherein said chamber is a first chamber and said diameter of said chamber is a first chamber diameter, said body further including a second chamber adjacent to said first chamber, said second chamber having a second chamber diameter greater than or equal to said diameter of said retention head.

11. A strap attachment assembly for an orthopedic brace comprising:
an anchor mounted on an orthopedic brace component, said anchor comprising a retention head, wherein said retention head has an outer boundary defining a diameter;
a strap retainer mounted on a strap, said strap retainer comprising a retention plate transitionable between a locked condition and an unlocked condition and including a retention opening formed in a surface of said retention plate, said retention opening having an inner boundary defining a diameter greater than or equal to said diameter of said retention head to retain said retention head in said retention opening when said retention plate is in said locked condition by positioning said inner boundary adjacent to said outer boundary of said retention head and blocking displacement of said outer boundary in a direction past said inner boundary and to release said retention head from said retention opening when said retention plate is in said unlocked condition by positioning said inner boundary clear of said outer boundary and permitting displacement of said outer boundary in said direction past said inner boundary; and
means for biasing said retention plate in said locked condition.

12. The strap attachment assembly of claim 11 wherein said biasing means is flexion of said retention plate.

13. The strap attachment assembly of claim 11 wherein said biasing means is said strap.

14. The strap attachment assembly of claim 11 wherein said surface of said retention plate has a raised portion adjacent to said retention opening.

15. The strap attachment assembly of claim 14 wherein said strap retainer further comprises a body including a first chamber having a first chamber diameter less than said diameter of said retention head and a second chamber adjacent to said first chamber, said second chamber having a second chamber diameter greater than or equal to said diameter of said retention head, wherein said first chamber is aligned with said retention opening and said second chamber is offset from said retention opening.

16. The strap attachment assembly of claim 15 wherein said second chamber is aligned with said raised portion.

17. The strap attachment assembly of claim 14 wherein said retention plate has a pivot point on said surface substantially opposite said raised portion, said pivot point pivotally engageable with said body when said raised portion is displaced away from said body.

18. The strap attachment assembly of claim 11 wherein said strap retainer further comprises a body including a first chamber having a first chamber diameter less than said diameter of said retention head and a second chamber adjacent to said first chamber, said second chamber having a second chamber diameter greater than or equal to said diameter of said retention head, wherein said first chamber is aligned with said retention opening and said second chamber is offset from said retention opening.

19. A method for connecting a strap to an orthopedic brace comprising:

provifing an anchor mounted on an orthopedic brace component, said anchor including a retention head having an outer boundary defining a diameter;

providing a strap retainer mounted on a strap, said strap retainer having a retention plate including a retention opening, said retention opening having an inner boundary defining a diameter greater than or equal to said diameter of said retention head;

positioning said outer boundary of said retention head adjacent to said inner boundary of said retention opening to block displacement of said outer boundary in a direction past said inner boundary, thereby defining a locked condition of said retention plate; and positioning said outer boundary clear of said inner boundary to permit displacement of said outer boundary in a direction past said inner boundary, thereby defining an unlocked condition of said retention plate, wherein said retention plate is biased in said locked condition.

20. The method of claim 19 wherein said outer boundary is positioned clear of said inner boundary by applying a force against a displacement point on a surface of said retention plate to rotate said retention plate about a pivot point on said surface substantially opposite said displacement point.

\* \* \* \* \*